United States Patent [19]

Berglund

[11] 4,332,768

[45] Jun. 1, 1982

[54] ARRANGEMENT FOR SUPPLYING METERED QUANTITIES OF REAGENT LIQUID TO THE TEST TUBES OF AN ANALYZING APPARATUS

[75] Inventor: Erling G. Berglund, Järfälla, Sweden

[73] Assignee: Clinicon AB, Bromma, Sweden

[21] Appl. No.: 237,076

[22] Filed: Feb. 23, 1981

[30] Foreign Application Priority Data

Mar. 11, 1980 [SE] Sweden ............................ 8001913

[51] Int. Cl.³ ..................... G01N 1/14; G01N 1/18
[52] U.S. Cl. ............................. 422/63; 73/864.34; 73/864.81; 73/864.83; 73/864.11; 422/100; 422/103
[58] Field of Search .............. 422/63, 81, 100, 103; 141/130; 73/864.34, 864.35, 864.81, 864.11, 863.83

[56] References Cited

U.S. PATENT DOCUMENTS

| 3,440,016 | 4/1969 | Serfass ............................ 422/81 |
| 3,948,607 | 4/1976 | Atwood et al. .................. 422/63 |
| 4,070,156 | 1/1978 | Moran et al. .................... 422/100 |
| 4,220,621 | 9/1980 | Simpson et al. ............. 422/100 X |
| 4,253,847 | 3/1981 | Matson et al. ................ 422/81 X |
| 4,302,421 | 11/1981 | Baker ............................ 422/63 X |

*Primary Examiner*—Ronald E. Serwin

*Attorney, Agent, or Firm*—Browdy and Neimark

[57] ABSTRACT

Figure 1:
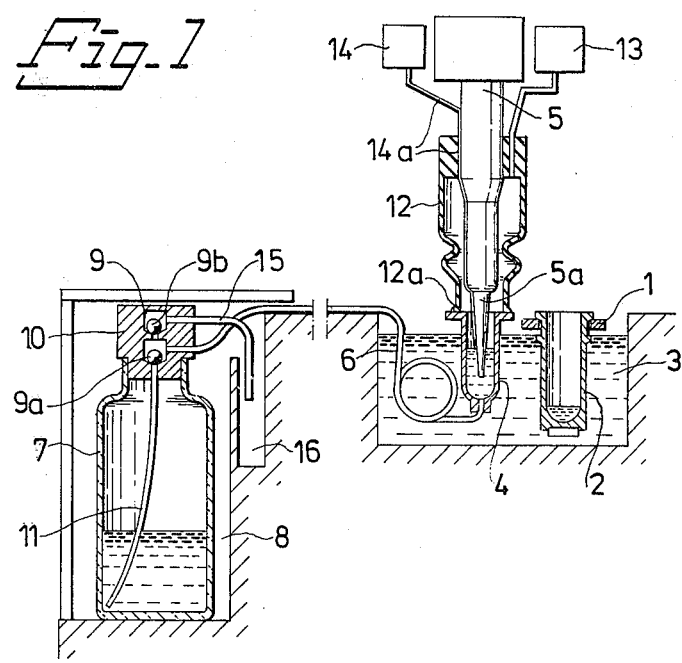

An arrangement for supplying metered quantities of reagent liquid to a test-tube in a clinical analyzing apparatus, includes a cup for reagent liquid and a pipetting pump which is movable between the reagent cup and the test-tube and which is able to withdraw by suction a given volume of reagent liquid from the reagent cup and dispense said volume of liquid into the test tube. The reagent liquid can be supplied to the cup from a storage vessel, by connecting a source of sub-pressure to the reagent cup and by withdrawing reagent liquid from the storage vessel by suction up into said cup through a line connecting the storage vessel with the cup. The sub-pressure is applied to the reagent cup by means of a bellow structure mounted on the pump so as to be moved into sealing abutment with the rim of the reagent cup when the pump is lowered thereinto. The bellow structure is connected to a source of sub-pressure. For the purpose of emptying and cleaning the reagent cup and the line passing thereto, the pump may be arranged to dispense water into said cup, the means arranged for connecting the reagent cup to a sub-pressure source being also arranged to alternatively connect a source of over-pressure to the reagent cup, so that reagent liquid and water can be forced out from the cup and the line connected thereto, to drain. (FIG. 1).

8 Claims, 2 Drawing Figures

U.S. Patent    Jun. 1, 1982    4,332,768

ARRANGEMENT FOR SUPPLYING METERED QUANTITIES OF REAGENT LIQUID TO THE TEST TUBES OF AN ANALYZING APPARATUS

The present invention relates to an arrangement in automatically operating clinical analyzing apparatus for supplying metered quantities of reagent liquid to one or more test tubes. A reagent-metering arrangement in automatic clinical analyzing apparatus is previously described, for example, in U.S. Pat. No. 3,758,274.

This prior art arrangement comprises a cup for liquid reagent and a pump capable of drawing liquid into a suction pipe and re-dispensing a given volume of said liquid from the suction pipe, said pump being movable between a position above the reagent cup and a position above a test tube and arranged to be lowered, in said first position, into the reagent cup for withdrawing reagent liquid therefrom and in said second position to dispense reagent liquid into the test tube.

One problem encountered with such reagent supply systems is associated with the fact that the test tubes are often immersed in a temperature regulating bath which maintains the contents of the test tubes at a suitable elevated temperature for the reaction between the samples and the reagents. The reagent liquid, which is supplied to the sample in a test tube by means of a metering pump, should be heated to said temperature before being introduced into the test tube, so that the effective reaction time can be accurately controlled. The durability of the reagent liquids at such temperatures is limited, however, and hence it would be to advantage if only a minor quantity of the reagent could be held in readiness at said elevated temperature and be replaced at the same rate as it is consumed, while the larger part of reagent liquid in the apparatus is kept at a lower temperature suitable for the durability of the reagent liquid, for example is kept in a cooled space. This would make it possible, to no disadvantage, to leave this store of reagent liquid in the cold space of the analyzing apparatus over those periods when the apparatus was not in use, for example overnight. In the case of an automatically working analyzing apparatus it would also be a great advantage if one and the same metering pump could be used to transfer several dissimilar reagent liquids to the test tubes selectively. It is difficult, however, within the limited working range of a single metering pump to find place for large quantities of a large number of differing reagent liquids. It would be an advantage also in this respect if only relatively small quantities of reagent liquid need be kept in readiness, at the desired elevated temperature, in the vicinity of the metering pump, i.e. within its working range, and the temperature-regulated quantities of reagent liquid could be replaced at the same rate at which they were used. When shutting down an analyzing apparatus of the kind described for a relatively long period of time, e.g. over night, it is necessary to empty the reagent cups cooperating with the metering pump and the supply lines to said cups of reagent liquid and to clean said cups and lines, since if left in these parts of the reagent supply system, which are at elevated temperature or room temperature and which are also partially in contact with the ambient air, the reagent liquid will be destroyed and part of said liquid will also dry into said cups and said supply lines. It should be possible to drain and cleanse the reagent supply system quickly and simply, preferably automatically, so that the work connected therewith is as little as possible.

The object of the present invention is to provide a reagent-supply arrangement of the aforedescribed kind which will fulfill the above desiderata.

According to the invention this is achieved with a reagent-supply arrangement of the aforedescribed kind in that the arrangement comprises additionally a storage vessel for reagent liquid, which is connected to the reagent cup through a line having its one end projecting into the liquid in the storage vessel and its other end discharging into the cup and including a check valve permitting a liquid flow in only one direction towards the reagent cup, means for generating a sub-pressure in the reagent cup, and a level sensing means for sensing the liquid level in the cup and rendering said sub-pressure generating means inoperative when the liquid level in the cup exceeds a given highest level.

Figure 2:
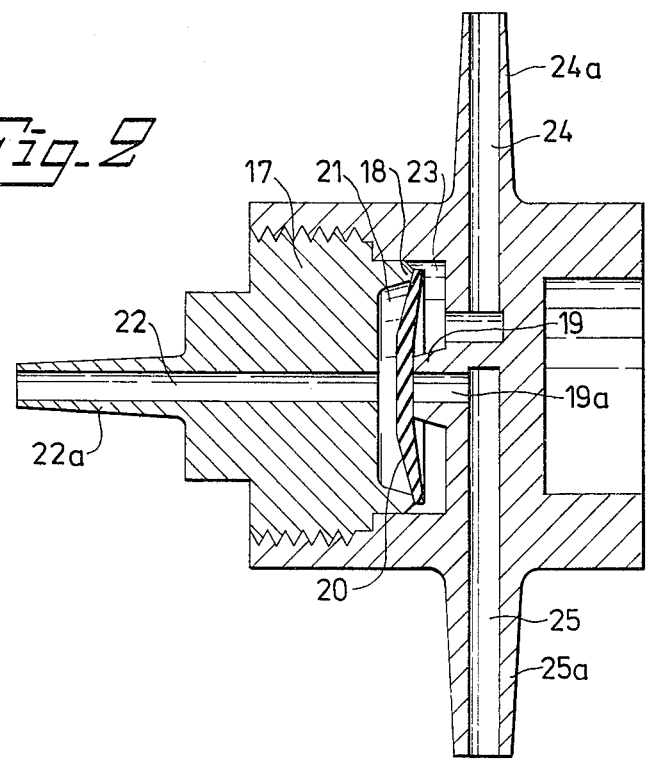

The invention and advantages afforded thereby as well as additional preferred features of the invention will now be described with reference to an exemplary embodiment thereof illustrated in the accompanying schematic drawing, in which FIG. 1 illustrates, partly in section, a reagent supply system according to the invention for an automatically operating clinical analyzing apparatus, and FIG. 2 illustrates in section an advantageous embodiment of a valve unit included in the system illustrated in FIG. 1.

The clinical analyzing apparatus, which is only partly shown in FIG. 1, includes a turntable 1 which is arranged for rotation about a vertical axis (not shown) and which has arranged around its periphery a plurality of holes in which test tubes are suspended. The test tubes 2 are arranged to be moved by the turntable 1 to a first supply station (not shown) for supplying a sample to respective test tubes and then to at least one second supply station, shown schematically in the Figure, for supplying a desired reagent liquid to the samples in the test tubes, and finally to a measuring station (not shown) in which a given property of the samples reacted with said reagent can be measured in a suitable fashion. The test tubes 2 depending from the turntable 1 extend down into a temperature regulating bath 3, which holds the test tubes and the contents thereof at a temperature suitable for the reaction in question.

Arranged at said second station, at which metered quantities of reagent liquid are fed to the samples in the test tubes 2, is at least one stationarily arranged cup 4 which is immersed in the bath 3 and which is able to hold only a relatively small quantity of reagent liquid. If it is to be possible to introduce several dissimilar reagent liquids selectively to the test tubes 2 a corresponding number of reagent cups 4 must be arranged adjacent one another in the bath 3, each of said reagent cups having its own particular reagent supply system constructed in the manner hereinafter described with reference to the cup 4 illustrated in FIG. 1. To enable given quantities of reagent liquid to be transferred from the cup 4 to the test tubes 2 there is provided an automatically working pipette or metering pump 5, which may, for example, have the design described in the European Patent Application No. 79850080.7. The metering pump may be arranged for movement, in a manner not clearly shown, between a position in which it is located above the reaction cup 4, or positions above each of a plurality of different reaction cups, and a position in which it is located above a test tube 2 in the table 1, when said test tube occupies a given location determined by rotation of said table. In the position above the cup 4, the suction pipe 5a of the pump 5 can be lowered into the reagent liquid present in the cup and be caused to draw up a given volume of liquid. When the pump 5 is located above a test tube 2, the pump can be caused to dispense a given volume of liquid into the tube. The operating mode of the pump 5 is described in more detail in the aforementioned European Patent Application. Because the reagent cup 4 is immersed in the temperature regulating bath, it is ensured that the reaction liquid transferred to the test tubes by the pump 5 has the correct temperature.

As before mentioned, the reagent cup 4 can only contain a relatively small amount of reagent liquid. Fresh reagent liquid must therefore be supplied to the cup at the same rate as liquid is taken therefrom by the pump. To this end the bottom of the cup 4 is connected to a hose 6 which passes to a reagent-liquid supply flask 7. The flask 7 is advantageously placed in a space 8 in the analyzing apparatus which can be held at a controlled low temperature suitable for storing the reagent liquid over a long period of time. The hose 6 is connected to a valve unit 9 arranged on the cap or stopper 10 of the flask 7. The valve unit 9 includes a first check valve 9a through which the hose 6 can be connected to a suction tube 11 extending down into the reagent liquid in the flask 7. The check valve 9a is arranged to permit liquid to flow in one direction only, from the flask 7 to the hose 6 and the cup 4. For the purpose of moving reagent liquid from the flask 7 to the cup 4 through the hose 6 a sub-pressure is created in the cup 4, under the effect of which reagent liquid is drawn by suction from the flask 7 through the tube 11, the check valve 9a, the hose 6 and into the cup 4. The sub-pressure is created in the reaction cup 4 at the same time as the pump 5 is lowered down thereinto to withdraw reagent liquid therefrom. To this end, the pump 5 is provided with resilient bellows 12 which are arranged coaxially around the suction pipe 5a of the pump 5 and the lower free edge 12a of which abuts the rim of the cup 4 when the pump 5 is lowered into said cup. The annular chamber surrounded by the bellows 12 communicates with a means 13 (only schematically illustrated) operative to apply a sub-pressure to the interior of the bellows 12 and therewith also to the cup 4, when the pump 5 is lowered into said cup and the bellows are in sealing engagement with the rim of the reagent cup. To ensure that a sufficient quantity of reagent liquid is metered to the cup 4, there is provided a suitable level sensor 14, which in the illustrated embodiment has a sensing electrode 14a mounted along the suction pipe 5a of the pump 5, in a manner such that the electrode is lowered into the cup 4 together with the pump. The level sensor 14 is arranged to act on the sub-pressure source 13 when the liquid in the cup 4 reaches a level at which the liquid reaches the sensing electrode 14a, in a manner to cause the sub-pressure in the bellows to cease, said bellows instead being connected to the surrounding atmosphere. In this way when the desired amount of reagent liquid has been fed to the cup 4, the supply of reagent liquid from the flask 7 to said cup is automatically stopped. The check valve 9a prevents reagent liquid from flowing back from the cup 4 to the flask 7. It will be understood that the cap 10 of the flask 7 must be designed to permit the interior of flask 7 to communicate with the surrounding atmosphere.

The hose 6 leading to the cup 4 is conveniently so laid in the bath 3, e.g. in the form of a helix, that the reagent liquid flowing through the hose has time to be heated to substantially the temperature of the bath before said liquid reaches the cup 4. In this way it is ensured that the liquid withdrawn by the pump 5 will always have the temperature desired.

As previously mentioned, it must be possible to drain the reagent cup 4 and the hose 6 of all reagent liquid and to cleanse said cup and hose of said liquid when the analyzing apparatus is to be shut-down for a prolonged period. In one particularly advantageous embodiment of the invention, the reagent cup 4 and the hose 6 can be automatically emptied of reagent liquid, by designing the sub-pressure device 13 to alternatively apply an overpressure to the bellows 12. As the pump 5 is lowered into the cup 4 to the position shown in the drawings and the sub-pressure device 13 is caused to connect the bellows 12 to a source of overpressure, the reagent liquid is forced out from the cup 4 and the line 6, through a further check valve 9b in the valve unit 9 and a drainage line 15 connected to said check valve 9b, to a suitable drain 16. The check valve 9b is arranged to permit liquid to flow in only one direction, from the hose 6 to the drainage line 15. As will be understood, the check valve 9a remains closed during this emptying process, similarly as the check valve 9b remains closed when reagent liquid is drawn from the storage flask 7 to the cup 4, in the manner previously described.

Subsequent to emptying the cup 4 and the hose 6 of reagent liquid in the manner described, the requisite cleansing of said cup and said hose can also be effected automatically by arranging in the vicinity of the cup 4 a further, similar cup (not shown) which contains water. In this case, the metering pump 5 is also arranged for movement to a position above the water cup, and to be lowered into said cup for withdrawing water therefrom. The pump 5 can then be moved to the reagent cup 4 so as to dispense said water therein, whereafter the sub-pressure device 13 is again caused to connect the bellows 12 to a source of overpressure, under the action of which the water is pressed out from the reagent cup, through the hose 6 and the check valve 9b, to the drain 16, thereby effectively cleaning the cup 4 and the hose 6. The process can, of course, be repeated a number of times, if so required.

FIG. 2 illustrates an advantageous embodiment of the valve unit 9 incorporated in the cap 10 of the flask 7. As shown in the figure, the valve unit comprises a valve housing 17 having a valve chamber in which two stationary, annular valve seats 18 and 19 are arranged concentrically with one another in substantially the same plane but facing in opposite directions, the valve seat 18 being larger than the valve seat 19. Mounted between the two valve seats 18 and 19 is a resilient diaphragm, which, as shown in the figure, is so arranged that the outer peripheral part of the diaphragm abuts the larger valve seat 18, while the centre part of the diaphragm abuts the smaller valve seat 19. Thus the diaphragm 20 divides the interior of the valve house 17 into a first chamber 21 which is connected to the suction tube 11 extending down in the storage flask 7, via a passage 22 and a hose connection 22a, and a second chamber 23 which is connected to the hose 6 leading to the reagent cup 4, via a pressure 24 and a hose connection 24a. The valve opening 19a encircled by the smaller valve seat 19 is connected to the line 15 passing to the drain 16, via a passage 25 and a hose connection 25a. The diaphragm 20 together with the larger valve seat 18 forms the check valve 9a illustrated in FIG. 1, while said diaphragm together with the valve seat 19 forms the illustrated check valve 9b. The pressure prevailing in the valve chamber 21 connected to the interior of the flask 7 is atmospheric pressure, as is also the pressure prevailing in the passage 25 of the valve housing connected to the drain line 15. When a sub-pressure is created in the passage 24, in the manner aforedescribed the diaphragm 20 is lifted from the valve seating 18 and reagent liquid can flow from the flask 7 to the reagent cup 4. When a source of overpressure is connected to the passage 24 in the valve housing 17 in the manner described for emptying and cleaning the reagent cup 4 and the hose 6, the diaphragm 20 is lifted from the seating 19, so that reagent liquid or water can be forced from the cup 4, through the hose 6 and out into the line 15 to the drain 16. This embodiment of the valve unit, which functions as a double-acting check valve, has the advantage of being very simple and reliable and can be arranged to open in response to very small differences in pressure, e.g. pressure differences in the order of some few tenths of a bar, while ensuring that the valve which is closed at that point of time is fully sealed.

It will be understood that an arrangement according to the invention can be constructed in a number of ways different to that of the described and illustrated embodiment, for example with respect to the design of the metering pump, the design and arrangement of the level sensor, the design of the device for connecting the reagent cup to a source of sub-pressure or over-pressure, and the design of the check valves. Thus, the valves need not necessarily be arranged in the cap of the flask 7. Neither need the level sensor be mounted on the pump to accompany the movements thereof, even though such an arrangement affords the advantage whereby it is not necessary to provide a separate sensor for each cup. For the same reason, it is an advantage to arrange the sub-pressure and overpressure generating device in the manner described above, although other arrangements can naturally be applied. An arrangement according to the invention for metering quantities of reagent liquid to one or more test tubes can, of course, also be applied with analyzing apparatus or instruments constructed differently to the described analyzing apparatus.

I claim:

1. An arrangement in an automatically operating analyzing apparatus for supplying metered quantities of liquid reagent to a test-tube, comprising a cup for liquid reagent; a pump capable of drawing liquid into a suction pipe and re-dispensing a given volume of liquid from said suction pipe, said pump being movable between a position above the reagent cup and a position above the test-tube and arranged to be lowered, in said first position, into the reagent cup for withdrawing reagent liquid therefrom and in said second position to dispense reagent liquid into the test-tube; a storage vessel for reagent liquid, said vessel being connected to said cup through a line having its one end projecting into the liquid in the storage vessel and its other end discharging into the cup, and including a check valve arranged to permit a liquid flow in only one direction towards the reagent cup; means for generating a sub-pressure in said cup; and a level sensing means for sensing the level of liquid in said cup and rendering said sub-pressure generating means inoperative when the vessel of liquid in said cup exceeds a given highest level.

2. An arrangement as claimed in claim 1, wherein said means for generating a sub-pressure in the reagent cup includes a bellow structure which is connected to a source of sub-pressure controllable by said level sensing means and which is mounted on the pump coaxially around the suction pipe in a manner such as to seal against the rim of the cup when the pump is lowered thereinto.

3. An arrangement as claimed in claim 1, wherein said level sensing means comprises a sensing element mounted on the pump in a manner to be lowered down into the cup together with said pump.

4. An arrangement as claimed in claim 1, comprising a cup for containing water, and wherein said pump is also arranged for movement to a position above said water-cup and to be lowered down thereinto for withdrawing water therefrom, and for movement subsequent thereto to the position above the reagent cup for dispensing said water thereinto; said means for generating a sub-pressure in the reagent cup being arranged to generate alternatively an over-pressure in said reagent cup; and said line discharging into the reagent cup being connected, via a second check valve permitting liquid flow in only one direction from the reagent cup, with a line passing to a drain.

5. An arrangement as claimed in claim 1, wherein said reagent cup is arranged in a temperature-regulating bath while said reagent storage vessel is arranged externally thereof; said line between the reagent storage vessel and the reagent cup having a length in said bath such that reagent liquid flowing from the storage vessel to the reagent cup is heated to substantially the temperature of the bath before reaching the reagent cup.

6. An arrangement as claimed in claim 1, wherein said reagent storage vessel is arranged in a space whose temperature can be controlled.

7. An arrangement as claimed in claim 4, wherein said two check valves form part of a valve unit including a valve housing with a valve chamber, in which two stationary annular valve seats are arranged concentrical relative to one another and facing in mutually opposite directions, and a resilient, diaphragm mounted between said valve seats so that the outer peripheral part of the diaphragm lies against the larger valve seat and the center part of the diaphragm lies against the smaller valve seat, said diaphragm dividing the valve chamber into two parts of which the part comprising the larger valve seat is connected with the reagent storage vessel and the part comprising the smaller valve seat is connected to the line passing to the reagent cup, while the valve opening encircled by the smaller valve seat is connected to the line passing to the drain.

8. An arrangement as claimed in claim 1 including a plurality of reagent cups with associated reagent storage vessels and line systems and valve systems for differing reagents, said pump being movable selectively to all of said reagent cups.

* * * * *